US011724253B2

(12) United States Patent
Fecant et al.

(10) Patent No.: US 11,724,253 B2
(45) Date of Patent: Aug. 15, 2023

(54) METHOD FOR THE PHOTOCATALYTIC REDUCTION OF CARBON DIOXIDE IMPLEMENTING A SUPPORTED PHOTOCATALYST MADE FROM MOLYBDENUM SULFIDE OR TUNGSTEN SULFIDE

(71) Applicant: IFP Energies nouvelles, Rueil-Malmaison (FR)

(72) Inventors: Antoine Fecant, Brignais (FR); Audrey Bonduelle-Skrzypczak, Francheville (FR); Ranin Atwi, Villeurbanne (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 583 days.

(21) Appl. No.: 16/764,131

(22) PCT Filed: Nov. 7, 2018

(86) PCT No.: PCT/EP2018/080513
§ 371 (c)(1),
(2) Date: May 14, 2020

(87) PCT Pub. No.: WO2019/096657
PCT Pub. Date: May 23, 2019

(65) Prior Publication Data
US 2020/0276572 A1    Sep. 3, 2020

(30) Foreign Application Priority Data
Nov. 15, 2017 (FR) ................... 17/60.718

(51) Int. Cl.
*B01J 37/00* (2006.01)
*B01J 37/34* (2006.01)
*B01J 19/12* (2006.01)
*B01J 27/051* (2006.01)
*B01J 35/00* (2006.01)
*B01J 37/02* (2006.01)
*B01J 37/20* (2006.01)

(52) U.S. Cl.
CPC .......... *B01J 37/345* (2013.01); *B01J 19/123* (2013.01); *B01J 19/127* (2013.01); *B01J 27/051* (2013.01); *B01J 35/004* (2013.01); *B01J 35/0006* (2013.01); *B01J 35/0033* (2013.01); *B01J 37/0203* (2013.01); *B01J 37/0236* (2013.01); *B01J 37/20* (2013.01)

(58) Field of Classification Search
None
See application file for complete search history.

(56) References Cited

U.S. PATENT DOCUMENTS

| | | | |
|---|---|---|---|
| 9,579,642 B2 | 2/2017 | Alphazan et al. | |
| 9,839,903 B2 | 12/2017 | Alphazan et al. | |
| 2014/0251786 A1* | 9/2014 | Landry | C07C 1/12 422/186 |
| 2015/0158017 A1* | 6/2015 | Fecant | B01J 37/0221 502/220 |

FOREIGN PATENT DOCUMENTS

| | | | | |
|---|---|---|---|---|
| FR | 3004967 A1 | 10/2014 | | |
| FR | 3004968 A1 | 10/2014 | | |
| WO | WO-2016058862 A1 * | 4/2016 | ......... | B01J 35/0006 |

OTHER PUBLICATIONS

James et al, synthesis and photocatalytic activity of the MoS2 and WS2 nanoparticles in degradation of organic compounds (Year: 2009).*
WO-2016058862-A1, English translation (Year: 2016).*
International Search report PCT/EP2018/080513 dated Dec. 11, 2018 (pp. 1-2).

* cited by examiner

*Primary Examiner* — Stefanie J Cohen
(74) *Attorney, Agent, or Firm* — Millen White Zelano and Branigan, PC; Csaba Henter

(57) ABSTRACT

The invention concerns a method for the photocatalytic reduction of carbon dioxide carried out in the liquid phase and/or in the gas phase under irradiation using a photocatalyst comprising a support made from alumina or silica or silica-alumina and nanoparticles of molybdenum sulfide or tungsten sulfide having a band gap greater than 2.3 eV, said method comprising the following steps: a) bringing a feedstock containing carbon dioxide and at least one sacrificial compound into contact with said photocatalyst, b) irradiating the photocatalyst with at least one source of irradiation producing at least one wavelength smaller than the width of the band gap of said photocatalyst so as to reduce the carbon dioxide and oxidise the sacrificial compound in the presence of said photocatalyst activated by said source of irradiation, in such a way as to produce an effluent containing, at least in part, C1 or above carbon-containing molecules, different from CO2.

20 Claims, No Drawings

METHOD FOR THE PHOTOCATALYTIC REDUCTION OF CARBON DIOXIDE IMPLEMENTING A SUPPORTED PHOTOCATALYST MADE FROM MOLYBDENUM SULFIDE OR TUNGSTEN SULFIDE

TECHNICAL FIELD OF THE INVENTION

The field of the invention is that of the photocatalytic reduction of carbon dioxide ($CO_2$) under irradiation by using a photocatalyst.

PRIOR ART

Fossil fuels, such as coal, oil and natural gas, are the main conventional energy sources in the world due to their availability, stability and high energy density. However, their combustion produces carbon dioxide emissions which are considered to be the main cause of global warming. Thus, there is a growing need to reduce $CO_2$ emissions, either by capturing said $CO_2$ or by converting it.

Although "passive" carbon capture and sequestration (CCS) is generally considered to be an effective process for reducing $CO_2$ emissions, other strategies can be envisioned, in particular "active" strategies for converting $CO_2$ into products with economic value, such as fuels and industrial chemicals.

Such active strategies are based on the reduction of carbon dioxide into exploitable products. The reduction of carbon dioxide can be carried out biologically, thermally, electrochemically or else photocatalytically.

Among these options, photocatalytic reduction of $CO_2$ is gaining increased attention since it can potentially consume alternative energy forms, for example by harnessing solar energy, which is abundant, inexpensive, and environmentally clean and safe.

Photocatalytic reduction of carbon dioxide makes it possible to obtain C1 or above carbon-based molecules, such as CO, methane, methanol, ethanol, formaldehyde, formic acid or else other molecules such as carboxylic acids, aldehydes, ketones or various alcohols. These molecules, such as methanol, ethanol, formic acid or else methane and all $C_{1^+}$ hydrocarbons can be directly useful in terms of energy. Carbon monoxide CO can also be exploited in terms of energy as a mixture with hydrogen for the formation of fuels by Fischer-Tropsch synthesis. The molecules of carboxylic acids, aldehydes, ketones or various alcohols can, for their part, find applications in chemical or petrochemical processes. All these molecules are therefore of great interest from an industrial point of view.

Photocatalytic reduction of carbon dioxide requires the use of semiconductors, which are capable of absorbing photons and of initiating redox reactions. A semiconductor is characterized by its bandgap. The bandgap corresponds to the energy difference between the valence and conduction bands of the materials. Any photon of energy greater than its bandgap can be absorbed by the semiconductor. Any photon of energy lower than its bandgap cannot be absorbed by the semiconductor.

Furthermore, it is known to those skilled in the art that the bandgap of the semiconductors in particle form varies depending on the size of these particles. The semiconductor bandgap increases for nanoparticle sizes which decrease to the one nanometer scale. This known physical phenomenon is called quantum size effect.

Processes for the photocatalytic reduction of carbon dioxide in the presence of a photocatalyst containing a sulfided molybdenum phase are known in the prior art.

Tu et al. (Nanoscale, 9 (26), p. 9065-9070, 2017) propose an $MoS_2$—$TiO_2$ hybrid compound for the photocatalytic reduction of $CO_2$ to methanol. However, the sulfided molybdenum phase plays the role of co-catalyst and does not participate in the absorption of photons allowing the reduction of $CO_2$ due to the low bandgap of this material. Only $TiO_2$ plays this role of semiconductor and thus involves photon absorption only in the ultraviolet range.

Zang et al. (Journal of Energy Chemistry, 25 (3), p. 500-506, 2016) propose, for their part, a hybrid solid based on $MoS_3$—$TiO_2$. Here also, the sulfided molybdenum phase plays the role of co-catalyst and is not capable of absorbing photons that are effective for the reduction of $CO_2$ due to the low bandgap of this material; it is again the $TiO_2$ which plays this role with again the constraint of only absorbing photons in the ultraviolet range.

On the other hand, nanoparticles of sulfided molybdenum having a bandgap greater than that of a mass sulfided molybdenum are known from the prior art. Indeed, Wilcoxon et al. (The Journal of physical Chemistry B, 103, p. 11-17, 1999) proposes the synthesis of colloidal suspensions of $MoS_2$ nanoparticles having a bandgap of 2.25 eV for average nanoparticle sizes of 4 nm, whereas $MoS_2$ nanoparticles for sizes greater than 10 nm have a bandgap much lower than 2.25 eV. These sulfurized nanoparticles of molybdenum have been used in photoassisted oxidation of organic compounds. Nevertheless, colloidal suspensions suffer from stability problems and high production cost problems.

SUBJECTS OF THE INVENTION

The object of the invention is to provide a new, sustainable and more effective way of producing exploitable carbon-based molecules by photocatalytic conversion of carbon dioxide by means of electromagnetic energy, using a photocatalyst comprising a support based on alumina or silica or silica-alumina and nanoparticles of molybdenum sulfide or of tungsten sulfide having a bandgap greater than 2.3 eV. The use of photocatalysts of this type for the photocatalytic reduction of $CO_2$ makes it possible to achieve improved performance qualities compared to the photocatalysts known for this reaction.

More particularly, the invention describes a process for photocatalytic reduction of carbon dioxide carried out in the liquid phase and/or in the gas phase under irradiation using a photocatalyst comprising a support based on alumina or silica or silica-alumina and nanoparticles of molybdenum sulfide or of tungsten sulfide having a bandgap greater than 2.3 eV, said process comprising the following steps:
 a) bringing a feedstock containing carbon dioxide and at least one sacrificial compound into contact with said photocatalyst,
 b) irradiating the photocatalyst with at least one irradiation source producing at least one wavelength smaller than the bandgap of said photocatalyst so as to reduce the carbon dioxide and to oxidize the sacrificial compound in the presence of said photocatalyst activated by said irradiation source, in such a way as to produce an effluent containing, at least partly, C1 or above carbon-based molecules other than $CO_2$.

The nanoparticles of molybdenum sulfide or tungsten sulfide having a bandgap greater than 2.3 eV advantageously absorb part of the visible spectrum of solar irradiation while allowing the reduction of carbon dioxide by suitable band levels, which does not allow the molybdenum or tungsten sulfide phases in the form of larger nanoparticles having a bandgap less than 2.3 eV. The use of said photocatalyst for the photocatalytic reduction of $CO_2$ thus makes it possible to exploit the visible part of the solar spectrum since it can absorb all photons of wavelength less than 620 nm (compared with 400 nm for a conventional photocatalyst of $TiO_2$ type).

In addition, these supported nanoparticles have the advantage of better stability with respect to colloidal suspensions.

According to one variant, and when the process is carried out in the gas phase, the sacrificial compound is a gaseous compound selected from water, ammonia, hydrogen, methane and an alcohol.

According to one variant, and when the process is carried out in the liquid phase, the sacrificial compound is a liquid compound selected from water, aqueous ammonia, an alcohol, an alidehyde or an amine.

According to one variant, a diluent fluid is present in steps a) and/or b).

According to one variant, the irradiation source is an artificial or natural irradiation source. According to one variant, the irradiation source emits at at least one wavelength range greater than 280 nm.

According to one variant, the porous support does not absorb photons of energy greater than 4 eV.

According to one variant, the content of molybdenum sulfide or of tungsten sulfide of the photocatalyst is between 4 and 50% by weight relative to the total weight of the photocatalyst.

According to one variant, the surface density which corresponds to the amount of molybdenum Mo atoms or of tungsten W atoms, deposited per unit surface area of support, is between 0.5 and 12 atoms of Mo or W per square nanometer of support. According to one variant, the photocatalyst is prepared according to a process comprising the following successive steps:

i) a step of impregnation by bringing a solution comprising an organic solvent A and at least one mononuclear precursor based on Mo or on W, denoted M, in their monomeric or dimeric form, having at least one M=O or M—OR bond or at least one M=S or M—SR bond where $R=C_xH_y$, where $x\geq 1$ and $(x-1)\leq y\leq(2x+1)$, into contact with a support based on alumina or silica or silica-alumina, advantageously previously calcined under vacuum or under an inert gas stream to remove the water possibly physisorbed on said support, ii) a maturing step, iii) a step of drying the impregnated support, at a temperature below 200° C., under an anhydrous atmosphere or under vacuum or under an inert gas stream, iv) a sulfurization step.

According to this variant, the molybdenum precursor is selected from the following compounds: $Mo(OEt)_5$, $Mo(OEt)_6$, $Mo(=O)(OEt)_4$, $Mo(=S)(OEt)_4$, $Mo(=S)(SEt)_4$, $Mo(=O)_2(OEt)_2$, $Mo(OC_6H_5)_6$, $Mo(SEt)_5$, $Mo(SEt)_6$, $Mo(OEt)(SEt)_4$, $Mo(OEt)_2(SEt)_3$, $Mo(OEt)_3(SEt)_2$, $Mo(OEt)_4(SEt)$, $Mo(=O)(OEt)_3(acac)$ with $Et=CH_2CH_3$ (ethyl group) and $acac=(CH_3COCHCOCH_3)$— (acetylacetonate) in their monomeric or dimeric form. According to this variant, the tungsten precursor is selected from the following compounds: $W(OEt)_5$, $W(OEt)_6$, $W(=O)(OEt)_4$, $W(=S)(OEt)_4$, $W(=S)(SEt)_4$, $W(=O)_2(OEt)_2$, $W(OC_6H_5)_6$, $W(SEt)_5$, $W(SEt)_6$, $W(OEt)_4(SEt)$, $W(OEt)_3(SEt)_2$, $W(OEt)_2(SEt)_3$, $W(OEt)(SEt)_4$, $W(=O)(OEt)_3(acac)$ with $Et=CH_2CH_3$ (ethyl group) and $acac=(CH_3COCHCOCH_3)$— (acetylacetonate), in their monomeric or dimeric form. Hereinafter, the groups of chemical elements are given according to the CAS classification (CRC Handbook of Chemistry and Physics, published by CRC Press, Editor in Chief D. R. Lide, 81st edition, 2000-2001). For example, Group VIII according to the CAS classification corresponds to the metals of columns 8, 9 and 10 according to the new IUPAC classification.

DETAILED DESCRIPTION OF THE INVENTION

Photocatalysis is based on the principle of activation of a semiconductor or a set of semiconductors such as the photocatalyst used in the process according to the invention, using the energy provided by the irradiation. Photocatalysis can be defined as the absorption of a photon, the energy of which is greater than or equal to the bandgap between the valence band and the conduction band, which induces the formation of an electron-hole pair in the semiconductor. There is therefore excitation of an electron at the level of the conduction band and formation of a hole on the valence band. This electron-hole pair will allow the formation of free radicals which will either react with compounds present in the medium or else recombine according to various mechanisms. Each semiconductor has an energy difference between its conduction band and its valence band, or "bandgap", which is specific to it.

A photocatalyst composed of one or more semiconductors can be activated by the absorption of at least one photon. Absorbable photons are those which the energy is greater than the bandgap of the semiconductors. In other words, the photocatalysts can be activated by at least one photon with a wavelength corresponding to the energy associated with the bandgaps of the semiconductors constituting the photocatalyst or with a lower wavelength. The maximum wavelength absorbable by a semiconductor is calculated using the following equation:

$$\lambda_{max} = \frac{h \times c}{E_g}$$

With $\lambda_{max}$ the maximum wavelength absorbable by a semiconductor (in m), h the Planck constant (4.13433559× $10^{-15}$ eV·s), c the speed of light in the vacuum (299 792 458 m·s$^{-1}$) and Eg the bandgap of the semiconductor (in eV).

The value of the bandgap of semiconductor materials is measured by diffuse reflection absorption spectroscopy as described by the Tauc method (J. Tauc, R. Grigorovici, and A. Vancu, Phys. Status Solidi, 1966, 15, p 627; J. Tauc, "Optical Properties of Solids", F. Abeles ed., North-Holland, 1972; E. A. Davis and N. F. Mott, Philos. Mag., 1970, 22 p 903).

The invention describes a process for photocatalytic reduction of carbon dioxide carried out in the liquid phase and/or in the gas phase under irradiation using a photocatalyst comprising a support based on alumina or silica or silica-alumina and nanoparticles of molybdenum sulfide or of tungsten sulfide having a bandgap greater than 2.3 eV, said process comprising the following steps:

a) bringing a feedstock containing carbon dioxide and at least one sacrificial compound into contact with said photocatalyst, b) irradiating the photocatalyst with at least one irradiation source producing at least one wavelength smaller than the bandgap of said photocatalyst so as to reduce the carbon dioxide and to oxidize the sacrificial compound in the presence of said photocatalyst activated by said irradiation source, in such a way as to produce an effluent containing, at least partly, C1 or above carbon-based molecules other than $CO_2$.

Step a) of the Process

According to step a) of the process according to the invention, a feedstock containing said carbon dioxide and at least one sacrificial compound is brought into contact with said photocatalyst.

The term "sacrificial compound" is intended to mean an oxidizable compound. The sacrificial compound may be in gaseous or liquid form.

The term "C1 or above carbon-based molecules" is intended to mean molecules resulting from the reduction of $CO_2$ containing one or more carbon atoms, with the exception of $CO_2$. Such molecules are, for example, CO, methane, methanol, ethanol, formaldehyde, formic acid or else other molecules such as hydrocarbons, carboxylic acids, aldehydes, ketones or various alcohols.

The process according to the invention can be carried out in the liquid phase and/or in the gas phase.

The feedstock treated according to the process is in gaseous, liquid or gaseous and liquid two-phase form.

When the feedstock is in gaseous form, the $CO_2$ is present in its gaseous form in the presence of all gaseous sacrificial compounds alone or as a mixture. The gaseous sacrificial compounds are oxidizable compounds such as water ($H_2O$), hydrogen ($H_2$), methane ($CH_4$) or else alcohols. Preferably, the gaseous sacrificial compounds are water or hydrogen. When the feedstock is in gaseous form, the $CO_2$ and the sacrificial compound can be diluted by a gaseous diluent fluid such as $N_2$ or Ar.

When the feedstock is in liquid form, it can be in the form of an organic or aqueous ionic liquid. The feedstock in liquid form is preferentially aqueous. In an aqueous medium, the $CO_2$ is then dissolved in the form of aqueous carbonic acid ($H_2CO_3$), of hydrogen carbonate or of carbonate. The sacrificial compounds are liquid oxidizable compounds, possibly obtained by solubilization of a solid, in the liquid feedstock, such as water ($H_2O$), alcohols, aldehydes, amines or aqueous ammonia. Preferably, the sacrificial compound is water. When the liquid feedstock is an aqueous solution, the pH is generally between 1 and 9, preferably between 2 and 7. Optionally, and in order to modulate the pH of the aqueous liquid feedstock, a basic or acidic agent can be added to the feedstock. When a basic agent is introduced, it is preferably selected from alkali or alkaline-earth metal hydroxides, or organic bases such as amines or aqueous ammonia. When an acidic agent is introduced, it is preferably selected from inorganic acids such as nitric, sulfuric, phosphoric, hydrochloric or hydrobromic acid, or organic acids such as carboxylic or sulfonic acids.

Optionally, when the liquid feedstock is aqueous, it can contain, in any amount, any solvated ion, such as for example $K^+$, $Li^+$, $Na^+$, $Ca^{2+}$, $Mg^{2+}$, $SO_4^{2-}$, $Cl^-$, $F^-$, $NO_3^{2-}$.

When the process is carried out in the liquid phase or in the gas phase, a diluent fluid, which is respectively liquid or gaseous, may be present in the reaction medium. The presence of a diluent fluid is not required for the implementation of the invention; however, it may be useful to add it to the feedstock in order to ensure the dispersion of the feedstock in the medium, the dispersion of the photocatalyst, a control for the adsorption of reagents/products at the surface of the photocatalyst, a control for photon absorption by the photocatalyst, the dilution of the products to limit their recombination and other parasitic reactions of the same type. The presence of a diluent fluid also makes it possible to control the temperature of the reaction medium which can thus compensate for the possible exo/endothermicity of the photocatalyzed reaction. The nature of the diluent fluid is selected such that its influence is neutral on the reaction medium or that its possible reaction does not harm the performing of the desired carbon dioxide reduction. By way of example, nitrogen or argon can be selected as gaseous diluent fluid.

The bringing of the feedstock containing the carbon dioxide into contact with the photocatalyst can be carried out by any means known to those skilled in the art. Preferably, the bringing of the carbon dioxide feedstock into contact with the photocatalyst is carried out in a flow-through fixed bed or in a swept fixed bed.

When the implementation is in a flow-through fixed bed, said photocatalyst is preferentially fixed within the reactor, and the feedstock containing the carbon dioxide to be converted in gaseous and/or liquid form is sent through the photocatalytic bed.

When the implementation is in a swept fixed bed, said photocatalyst is preferentially fixed within the reactor, and the feedstock containing the carbon dioxide to be converted in gaseous and/or liquid form is sent over the photocatalytic bed.

When the implementation is in a fixed bed or in a swept bed, the implementation can be carry out continuously.

The photocatalytic process according to the invention uses a photocatalyst comprising a support and nanoparticles of molybdenum sulfide or tungsten sulfide having a bandgap greater than 2.3 eV.

The content of molybdenum sulfide or of tungsten sulfide of the photocatalyst is between 4 and 50% by weight relative to the total weight of the photocatalyst, and preferably between 5 and 25% by weight.

The surface density which corresponds to the amount of molybdenum Mo atoms or of tungsten W atoms, deposited per unit surface area of support, is advantageously between 0.5 and 12 atoms of Mo or of W per square nanometer of support, and preferably between 1 and 7 atoms of Mo or of W per square nanometer of support.

The photocatalyst according to the invention comprises a support based on alumina or silica or silica-alumina. According to one variant, the porous support does not absorb photons of energy greater than 4 eV.

When the support of said catalyst is based on alumina, it contains more than 50% of alumina and, in general, it contains only alumina or silica-alumina as defined below.

In another preferred case, the support of said catalyst is a silica-alumina containing at least 50% by weight of alumina. The content of silica in the support is at most 50% by weight, usually less than or equal to 45% by weight, preferably less than or equal to 40%.

When the support of said catalyst is based on silica, it contains more than 50% by weight of silica and, generally, it contains only silica.

According to one particularly preferred variant, the support consists of alumina, silica or silica-alumina.

Preferably, the support is based on alumina, and particularly preferably the support consists of alumina.

The alumina can be a transition alumina, for example an alpha phase alumina, a delta phase alumina, a gamma phase alumina or a mixture of alumina of these different phases.

According to one variant, the support has a specific surface area (measured according to standard ASTM D 3663-78 established from the Brunauer, Emmett, Teller method, i.e. the BET method, as defined in S. Brunauer, P. H. Emmett, E. Teller, J. Am. Chem. Soc., 1938, 60 (2), pp 309-319) of between 10 and 1000 m²/g, preferably between 50 and 600 m²/g.

The photocatalyst comprising a support and nanoparticles of molybdenum sulfide or of tungsten sulfide having a bandgap greater than 2.3 eV is prepared by the process described in documents FR 3 004 967 (for Mo) and FR 3 004 968 (for W) and comprises the following successive steps:
  i) a step of impregnation by bringing a solution comprising an organic solvent A and at least one mononuclear precursor based on Mo or on W, denoted M, in their monomeric or dimeric form, having at least one M=O or M—OR bond or at least one M=S or M—SR bond where $R=C_xH_y$, where $x \geq 1$ and $(x-1) \leq y \leq (2x+1)$, into contact with a porous support, advantageously previously calcined under vacuum or under an inert gas stream to remove the water possibly physisorbed on said support,
  ii) a maturing step,
  iii) a step of drying the impregnated support, at a temperature below 200° C., under an anhydrous atmosphere or under vacuum or under an inert gas stream,
  iv) a sulfurization step.

The process for preparing the photocatalyst makes it possible to obtain nanoparticles of molybdenum sulfide or of tungsten sulfide having a bandgap greater than 2.3 eV; this bandgap value corresponds to particle sizes of less than 3.5 nm.

The nanoparticles of molybdenum sulfide or of tungsten sulfide are defined by their empirical formula: $MoS_x$ such that $x=2$ or $3$.

The photocatalyst can also comprise nanoparticles of molybdenum oxysulfides or of tungsten oxysulfides. These nanoparticles are defined by their empirical formula $MoO_yS_z$ such that $0 < y+z < 5$ with y and z strictly positive integers.

Step i), termed step of bringing the solution into contact with the support, is an impregnation. Impregnations are well known to those skilled in the art. The impregnation method according to the invention is selected from dry impregnation, excess impregnation and successive impregnations. The "dry impregnation" method is advantageously used.

The organic solvent A used in step i) is generally an alkane, an alcohol, an ether, a ketone, a chlorinated solvent or an aromatic compound. Cyclohexane and n-hexane are preferably used.

The mononuclear precursor based on Mo or on W (denoted M), used in its monomeric or dimeric form, according to the invention advantageously has the formula $M(=O)n(=S)n'(OR)a(SR')b(L1)c(L2)d(L3)e(L4)f(L5)g$
  wherein $R=C_xH_y$ wherein $x \geq 1$ and $(x-1) \leq y \leq (2x+1)$,
  wherein $R'=C_{x'}H_{y'}$ wherein $x' \geq 1$ and $(x'-1) \leq y' \leq (2x'+1)$,
  wherein $0 \leq n+n' \leq 2$ and $0 \leq n \leq 2$ and $0 \leq n' \leq 2$,
  wherein, if $n=n'=0$, then $(a \neq 0$ or $b \neq 0)$ and $[(a+b+c+d+e+f+g=6$ and $0 \leq a \leq 6$, $0 \leq b \leq 6$, $0 \leq c \leq 6$, $0 \leq d \leq 6$, $0 \leq e \leq 6$, $0 \leq f \leq 6$, $0 \leq g \leq 6$, or $(a+b+c+d+e+f+g=5$ and $0 \leq a \leq 5$, $0 \leq b \leq 5$, $0 \leq c \leq 5$, $0 \leq d \leq 5$, $0 \leq e \leq 5$, $0 \leq f \leq 5$, $0 \leq g \leq 5)$, or $(a+b+c+d+e+f+g=4$ and $0 \leq a \leq 4$, $0 \leq b \leq 4$, $0 \leq c \leq 4$, $0 \leq d \leq 4$, $0 \leq e \leq 4$, $0 \leq f \leq 4$, $0 \leq g \leq 4)]$
  wherein, if $[(n=1$ and $n'=0)$ or $(n'=1$ and $n=0)]$, then $[a+b+c+d+e+f+g=4$ and a 4, $0 \leq b \leq 4$, $0 \leq c \leq 4$, $0 \leq d \leq 4$, $0 \leq e \leq 4$, $0 \leq f \leq 4$, $0 \leq g \leq 4)]$ or $[(a+b+c+d+e+f+g=3$ and $0 \leq a \leq 3$, $0 \leq b \leq 3$, $0 \leq c \leq 3$, $0 \leq d \leq 3$, $0 \leq e \leq 3$, $0 \leq f \leq 3$, $0 \leq g \leq 3)]$
  wherein, if $[n+n'=2$ and $0 \leq n \leq 2$ and $0 \leq n' \leq 2]$, then $(a+b+c+d+e+f+g=2$ and $0 \leq a \leq 2$, $0 \leq b \leq 2$, $0 \leq c \leq 2$, $0 \leq d \leq 2$, $0 \leq e \leq 2$, $0 \leq f \leq 2$, $0 \leq g \leq 2)$ with (L1), (L2), (L3), (L4) and (L5) ligands well known to those skilled in the art and of the type THF, dimethyl ether, dimethyl sulfide, $P(CH_3)_3$, allyl, aryl, halogenated compounds (selected from fluorinated compounds, chlorinated compounds, brominated compounds, amine, acetate, acetylacetonate, halide, hydroxide, —SH, etc. Preferably, the ligands are selected from acetylacetonate, THF and dimethyl ether.

Preferably, the precursors according to the invention do not contain any ligand (L1), (L2), (L3), (L4) and (L5).

Preferably, the molybdenum precursors according to the invention are selected from the following compounds: $Mo(OEt)_5$, $Mo(OEt)_6$, $Mo(=O)(OEt)_4$, $Mo(=S)(OEt)_4$, $Mo(=S)(SEt)_4$, $Mo(=O)_2(OEt)_2$, $Mo(OC_6H_5)_6$, $Mo(SEt)_5$, $Mo(SEt)_6$, $Mo(OEt)(SEt)_4$, $Mo(OEt)_2(SEt)_3$, $Mo(OEt)_3(SEt)_2$, $Mo(OEt)_4(SEt)$, $Mo(=O)(OEt)_3(acac)$ with $Et=CH_2CH_3$ (ethyl group) and $acac=(CH_3COCHCOCH_3)$— (acetylacetonate) in their monomeric or dimeric form.

Even more preferably, the molybdenum precursor is $Mo(OEt)_5$.

Preferably, the tungsten precursors according to the invention are selected from the following compounds: $W(OEt)_5$, $W(OEt)_6$, $W(=O)(OEt)_4$, $W(=S)(OEt)_4$, $W(=S)(SEt)_4$, $W(=O)_2(OEt)_2$, $W(OC_6H_5)_6$, $W(SEt)_5$, $W(SEt)_6$, $W(OEt)_4(SEt)$, $W(OEt)_3(SEt)_2$, $W(OEt)_2(SEt)_3$, $W(OEt)(SEt)_4$, $W(=O)(OEt)_3(acac)$ with $Et=CH_2CH_3$ (ethyl group) and $acac=(CH_3COCHCOCH_3)$— (acetylacetonate), in their monomeric or dimeric form. Very preferably, the tungsten precursors according to the invention are $W(OEt)_5$ or $W(OEt)_6$.

Step ii) is a maturation step intended to allow the entities to diffuse to the heart of the support. It is advantageously carried out under an anhydrous atmosphere (without water), preferably for between 30 minutes and 24 hours at ambient temperature. The atmosphere must preferably be anhydrous so as not to polycondense the previously impregnated precursors.

The drying carried out during step iii) is intended to remove the impregnation solvent A. The atmosphere must preferably be anhydrous (without water) so as not to polycondense said precursors previously impregnated. The temperature must not exceed 200° C. in order to keep intact said precursors grafted or deposited on the surface of the support. Preferably, the temperature will not exceed 120° C. Very preferably, the drying is carried out under vacuum, at ambient temperature. This step can alternatively be carried out by passing an inert gas stream.

The sulfurization step iv) can advantageously be carried out using a $H_2S/H_2$ or $H_2S/N_2$ gas mixture containing at least 5% by volume of $H_2S$ in the mixture at a temperature greater than or equal to ambient temperature, under a total pressure greater than or equal to 1 bar (0.1 MPa) for at least 2 h. Preferably, the sulfurization temperature is less than 350° C. Very preferably, the sulfurization temperature is less than 200° C. The sulfurization step iv) is intended to obtain the photocatalyst based on molybdenum sulfide or tungsten sulfide.

Step b) of the Process

According to step b) of the process according to the invention, the photocatalyst is irradiated with at least one irradiation source producing at least photons of wavelength less than 540 nm or of energy greater than 2.3 eV (that is to say the minimum bandgap of the photocatalyst), so as to reduce the carbon dioxide and to oxidize the sacrificial compound in the presence of said photocatalyst activated by said irradiation source, so as to produce an effluent containing, at least partly, C1 or above carbon-based molecules other than $CO_2$.

Any irradiation source emitting at least one wavelength suitable for activating said photocatalyst, that is to say absorbable by the photocatalyst, can be used according to the invention. It is possible for example to use natural solar irradiation or an artificial radiation source of laser, Hg, incandescent lamp, fluorescent tube, plasma or light-emitting diode (LED) type. Preferably, the irradiation source is solar irradiation.

The irradiation source produces radiation of which at least some of the wavelengths are less than the maximum wavelength ($\lambda_{max}$=540 nm) that can be absorbed by the nanoparticles of molybdenum sulfide or of tungsten sulfide constituting the photocatalyst according to the invention. When the irradiation source is solar irradiation, it generally emits in the ultraviolet, visible and infrared spectrum, i.e. it emits a wavelength range from 280 nm to 2500 nm approximately (according to the standard ASTM G173-03). Preferably, the source emits at at least in a wavelength range greater than 280 nm, very preferably from 315 nm to 800 nm, which includes the UV spectrum and/or the visible spectrum.

The irradiation source provides a stream of photons which irradiates the reaction medium containing the photocatalyst. The interface between the reaction medium and the light source varies according to the applications and the nature of the light source.

In one preferred embodiment, when solar irradiation is involved, the irradiation source is located outside the reactor and the interface between the two can be an optical window made of pyrex, quartz, organic glass or any other interface allowing the photons absorbable by the photocatalyst according to the invention to diffuse from the external medium into the reactor.

The realization of the photocatalytic reduction of carbon dioxide is conditioned by the supply of photons suitable for the photocatalytic system for the envisioned reaction and therefore is not limited to a specific pressure or temperature range outside those which make it possible to ensure the stability of the product(s). The temperature range used for the photocatalytic reduction of the feedstock containing the carbon dioxide is generally from −10° C. to +200° C., preferably from 0 to 150° C., and very preferably from 0 to 100° C. The pressure range used for the photocatalytic reduction of the feedstock containing the carbon dioxide is generally from 0.01 MPa to 70 MPa (0.1 to 700 bar), preferably from 0.1 to 2 MPa (1 to 20 bar).

The effluent obtained after the carbon dioxide photocatalytic reduction reaction contains, on the one hand, at least one C1 or above molecule other than carbon dioxide resulting from the reaction and, on the other hand, the unreacted feedstock, and also the possible diluent fluid, but also parallel reaction products such as for example dihydrogen resulting from the photocatalytic reduction of $H_2O$ when this compound is used as a sacrificial compound.

The use of the photocatalyst in a process for photocatalytic reduction of $CO_2$ makes it possible to absorb the visible part of the solar spectrum, and thus to exploit a significant proportion of the incident solar energy.

The following examples illustrate the invention.

EXAMPLES

Example 1: Photocatalyst a (not in Accordance with the Invention) $MoS_2$

Photocatalyst A is a commercial $MoS_2$-based semiconductor in powder form (Aldrich™, purity 99%). The bandgap of photocatalyst A is measured by diffuse reflection absorption spectrometry at 1.71 eV.

Example 2: Photocatalyst B (not in Accordance with the Invention) $WS_2$

Photocatalyst B is a commercial $WS_2$-based semiconductor in powder form (Aldrich™, purity 99%). The bandgap of photocatalyst B is measured by diffuse reflection absorption spectrometry at 1.56 eV.

Example 3: Photocatalyst C (in Accordance with the Invention) $MoS_x/Al_2O_3$

A γ alumina (γ-$Al_2O_3$) support is charged to a quartz reactor and calcined for 6 h at 300° C. with a temperature increase gradient of 5° C./min, then placed under vacuum ($10^{-5}$ mbar) at the same temperature for 16 h. The dehydroxylated support is then removed from the vacuum line and is cooled to 140° C. and then stored in a glove box. The specific surface area of the alumina support is 284 m²/g.

The molybdenum precursor is molybdenum pentaethoxide $Mo(OC_2H_5)_5$ (Gelest™ 90%). Dry degassed cyclohexane is used as the solvent. 1.96 ml of impregnation solution, prepared from 0.67 g of precursor and cyclohexane, are impregnated onto 2.58 g of dry support on a synthesis ramp using Schlenk devices. The impregnation of the support by the impregnation solution is carried out using a needle from one Schlenk device to the other.

The amount of molybdenum is adjusted so as to obtain approximately 1.7 Mo/nm², i.e. a weight content of Mo of 8%. After 15 hours of maturation, the extrudates are dried under vacuum ($10^{-5}$ mbar) for 2 hours at ambient temperature. After 16 h of maturation, the solid is subjected to 2 drying cycles under vacuum at ambient temperature, first by the Schlenk line (~$8.10^{-2}$ mbar) for 1 h and then by the high-vacuum line at $10^{-5}$ mbar for 1 h. Finally, the solid is subjected to a sulfurization step carried out at 100° C. with a flow rate of $H_2S/H_2$ gas (15/85 vol) of 2 l/h/g. The XPS analysis shows that 60% of the molybdenum is surrounded by sulfur. The bandgap of photocatalyst C is measured by diffuse reflection absorption spectrometry at 3.18 eV.

Example 4: Photocatalyst D (in Accordance with the Invention) $MoS_x/Al_2O_3$

Photocatalyst D is prepared identically to photocatalyst C, only the sulfurization step differs, with a treatment temperature at 200° C.

The XPS analysis gives an 87% molybdenum sulfurization. The bandgap of photocatalyst D is measured by diffuse reflection absorption spectrometry at 2.49 eV.

Example 5: Photocatalyst E (in Accordance with the Invention) $WS_x/Al_2O_3$

A γ alumina (γ-$Al_2O_3$) support is charged to a quartz reactor and calcined for 6 h at 300° C. with a temperature increase gradient of 5° C./min, then placed under vacuum ($10^{-5}$ mbar) at the same temperature for 16 h. The dehydroxylated support is then removed from the vacuum line and is cooled to 140° C. and then stored in a glove box. The specific surface area of the alumina support is 284 m²/g.

The treated alumina support (γ-$Al_2O_3$) and a tungsten(V) pentaethoxide—$W(OEt)_5$ liquid precursor (Gelest™, 90%) are inserted into separate Schlenk flasks. The flasks were then sealed and transferred onto the Schlenk line. The tungsten precursor is diluted with dried degassed cyclohexane so as to obtain an impregnation solution. This organic solution is prepared in such a way as to obtain a degree of W loading of 1.7 atoms/nm², i.e. a weight content of W of 5.5%. The impregnation of this precursor on the support is carried out using the needle.

After 16 h of maturation, the solid is subjected to 2 drying cycles under vacuum at ambient temperature, first by the Schlenk line (~8.10⁻² mbar) for 1 h and then by the high-vacuum line at 10⁻⁵ mbar for 1 h. Finally, the solid is subjected to a sulfurization step carried out at 150° C. with a flow rate of $H_2S/H_2$ gas (15/85 vol) of 2 l/h/g. The XPS analysis gives a 75% tungsten sulfurization. The bandgap of photocatalyst E is measured by diffuse reflection absorption spectrometry at 2.71 eV.

Example 6: Use of the Photocatalysts in Gas-Phase Photocatalytic Reduction of $CO_2$ Photocatalysts A, B, C, D and E are subjected to a gas-phase $CO_2$ photocatalytic reduction test in a continuous steel flow-through bed reactor equipped with a quartz optical window and a frit in front of the optical window on which the photocatalytic solid is deposited.

A sufficient amount of powder is deposited on the frit so as to cover the entire irradiated surface of the reactor (approximately 100 mg). The irradiated geometric surface area for all the photocatalysts is $8.042477 \times 10^{-04}$ m². The tests are carried out at ambient temperature under atmospheric pressure. A $CO_2$ flow rate of 0.3 ml/min passes through a water saturator before being dispensed into the reactor. The production of $CH_4$ resulting from the reduction of the carbon dioxide is monitored by analysis of the effluent every 6 minutes by micro gas chromatography. The UV-Visible irradiation source is provided by an Xe—Hg lamp (Asahi™, MAX302™). The irradiation power is always maintained at 80 W/m² for a wavelength range of between 315 and 400 nm. The duration of the test is 20 hours.

The photocatalytic activities are expressed in micromoles (μmol) of methane produced per hour and per m² irradiated. These are average activities over the entire duration of the tests. The results are reported in table 1 (below)

TABLE 1

Performance qualities of the photocatalysts relative to their average activity for the production of methane from a mixture of $CO_2$ and $H_2O$ in the gas phase

| Photocatalyst | | Average activity $CH_4$ (μmol/h/m²) | Average activity $CH_4$ (μmol/h/g) |
|---|---|---|---|
| A (not in accordance with the invention) | Commercial $MoS_2$ | 0 | 0 |
| B (not in accordance with the invention) | Commercial $WS_2$ | 0 | 0 |
| C (in accordance with the invention) | $MoS_x/Al_2O_3$ | 6.0 | 0.13 |
| D (in accordance with the invention) | $MoS_x/Al_2O_3$ | 2.5 | 0.05 |
| E (in accordance with the invention) | $WS_x/Al_2O_3$ | 5.7 | 0.11 |

The activity values show that the use of the solids according to the invention allows the photocatalytic reduction of carbon dioxide to $CH_4$.

The invention claimed is:

1. A process for photocatalytic reduction of carbon dioxide carried out in the liquid phase and/or in the gas phase under irradiation using a photocatalyst comprising a support based on alumina or silica or silica-alumina and nanoparticles of molybdenum sulfide or of tungsten sulfide having a bandgap greater than 2.3 eV, said process comprising the following steps:
   a) bringing a feedstock containing carbon dioxide and at least one sacrificial compound into contact with said photocatalyst,
   b) irradiating the photocatalyst with at least one irradiation source producing at least one wavelength smaller than the bandgap of said photocatalyst so as to reduce the carbon dioxide and to oxidize the sacrificial compound in the presence of said photocatalyst activated by said irradiation source, in such a way as to produce an effluent containing, at least partly, C1 or above carbon-based molecules other than $CO_2$,
   wherein the content of molybdenum sulfide or of tungsten sulfide of the photocatalyst is between 4 and 50% by weight relative to the total weight of the photocatalyst.

2. The process as claimed in claim 1, wherein, when it is carried out in the gas phase, the sacrificial compound is a gaseous compound selected from water, ammonia, hydrogen, methane and an alcohol.

3. The process as claimed in claim 1, wherein, when it is carried out in the liquid phase, the sacrificial compound is a liquid compound selected from water, aqueous ammonia, an alcohol, an aldehyde and an amine.

4. The process as claimed in claim 1, wherein a diluent fluid is present in steps a) and/or b).

5. The process as claimed in claim 1, wherein the irradiation source is an artificial or natural irradiation source.

6. The process as claimed in claim 1, wherein the irradiation source emits at at least one wavelength range greater than 280 nm.

7. The process as claimed in claim 1, wherein the porous support does not absorb photons of energy greater than 4 eV.

8. The process as claimed in claim 1, wherein the content of molybdenum sulfide or of tungsten sulfide of the photocatalyst is between 5 and 25% by weight relative to the total weight of the photocatalyst.

9. The process as claimed in claim 1, wherein the surface density which corresponds to the amount of molybdenum Mo atoms or of tungsten W atoms, deposited per unit surface area of support, is between 0.5 and 12 atoms of Mo or W per square nanometer of support.

10. The process as claimed in claim 1, wherein the photocatalyst is prepared according to a process comprising the following successive steps:
   i) a step of impregnation by bringing a solution comprising an organic solvent A and at least one mononuclear precursor based on Mo or on W, denoted M, in their monomeric or dimeric form, having at least one M=O or M—OR bond or at least one M=S or M—SR bond where $R=C_xH_y$ where $x \geq 1$ and $(x-1) \leq y \leq (2x+1)$, into contact with a support based on alumina or silica or silica-alumina, advantageously previously calcined under vacuum or under an inert gas stream to remove the water possibly physisorbed on said support,
   ii) a maturing step,
   iii) a step of drying the impregnated support, at a temperature below 200° C., under an anhydrous atmosphere or under vacuum or under an inert gas stream,
   iv) a sulfurization step.

11. The process as claimed in claim 10, wherein the molybdenum precursor is selected from the following compounds: $Mo(OEt)_5$, $Mo(OEt)_6$, $Mo(=O)(OEt)_4$, $Mo(=S)(OEt)_4$, $Mo(=S)(SEt)_4$, $Mo(=O)_2(OEt)_2$, $Mo(OC_6H_5)_6$, Mo(SEt)$_5$, Mo(SEt)$_6$, Mo(OEt)(SEt)$_4$, Mo(OEt)$_2$(SEt)$_3$, Mo(OEt)$_3$(SEt)$_2$, Mo(OEt)$_4$(SEt), Mo(=O)(OEt)$_3$(acac) with Et=CH$_2$CH$_3$ (ethyl group) and acac=(CH$_3$COCHCOCH$_3$)— (acetylacetonate) in their monomeric or dimeric form.

12. The process as claimed in claim 10, wherein the tungsten precursor is selected from the following compounds: W(OEt)$_5$, W(OEt)$_6$, W(=O)(OEt)$_4$, W(=S)(OEt)$_4$, W(=S)(SEt)$_4$, W(=O)$_2$(OEt)$_2$, W(OC$_6$H$_5$)$_6$, W(SEt)$_5$, W(SEt)$_6$, W(OEt)$_4$(SEt), W(OEt)$_3$(SEt)$_2$, W(OEt)$_2$(SEt)$_3$, W(OEt)(SEt)$_4$, W(=O)(OEt)$_3$(acac) with Et=CH$_2$CH$_3$ (ethyl group) and acac=(CH$_3$COCHCOCH$_3$)— (acetylacetonate), in their monomeric or dimeric form.

13. A process for photocatalytic reduction of carbon dioxide carried out in the liquid phase and/or in the gas phase under irradiation using a photocatalyst comprising a support based on alumina or silica or silica-alumina and nanoparticles of molybdenum sulfide or of tungsten sulfide having a bandgap greater than 2.3 eV, said process comprising the following steps:
   a) bringing a feedstock containing carbon dioxide and at least one sacrificial compound into contact with said photocatalyst,
   b) irradiating the photocatalyst with at least one irradiation source producing at least one wavelength smaller than the bandgap of said photocatalyst so as to reduce the carbon dioxide and to oxidize the sacrificial compound in the presence of said photocatalyst activated by said irradiation source, in such a way as to produce an effluent containing, at least partly, C1 or above carbon-based molecules other than CO$_2$, wherein
the photocatalyst is prepared according to a process comprising the following successive steps:
   i) a step of impregnation by bringing a solution comprising an organic solvent A and at least one mononuclear precursor based on Mo or on W, denoted M, in their monomeric or dimeric form, having at least one M=O or M—OR bond or at least one M=S or M—SR bond where R=C$_x$H$_y$, where x≥1 and (x−1)≤y≤(2x+1), into contact with a support based on alumina or silica or silica-alumina, advantageously previously calcined under vacuum or under an inert gas stream to remove the water possibly physisorbed on said support,
   ii) a maturing step,
   iii) a step of drying the impregnated support, at a temperature below 200° C., under an anhydrous atmosphere or under vacuum or under an inert gas stream,
   iv) a sulfurization step.

14. A process for photocatalytic reduction of carbon dioxide carried out in the liquid phase and/or in the gas phase under irradiation using a photocatalyst comprising a support based on alumina or silica or silica-alumina and nanoparticles of molybdenum sulfide or of tungsten sulfide having a bandgap greater than 2.3 eV, said process comprising the following steps:
   a) bringing a feedstock containing carbon dioxide and at least one sacrificial compound into contact with said photocatalyst,
   b) irradiating the photocatalyst with at least one irradiation source producing at least one wavelength smaller than the bandgap of said photocatalyst so as to reduce the carbon dioxide and to oxidize the sacrificial compound in the presence of said photocatalyst activated by said irradiation source, in such a way as to produce an effluent containing, at least partly, C1 or above carbon-based molecules other than CO$_2$, wherein
the surface density which corresponds to the amount of molybdenum Mo atoms or of tungsten W atoms, deposited per unit surface area of support, is between 0.5 and 12 atoms of Mo or W per square nanometer of support;

or
the molybdenum precursor is selected from the following compounds: Mo(OEt)$_5$, Mo(OEt)$_6$, Mo(=O)(OEt)$_4$, Mo(=S)(OEt)$_4$, Mo(=S)(SEt)$_4$, Mo(=O)$_2$(OEt)$_2$, Mo(OC$_6$H$_5$)$_6$, Mo(SEt)$_5$, Mo(SEt)$_6$, Mo(OEt)(SEt)$_4$, Mo(OEt)$_2$(SEt)$_3$, Mo(OEt)$_3$(SEt)$_2$, Mo(OEt)$_4$(SEt), Mo(=O)(OEt)$_3$(acac) with Et=CH$_2$CH$_3$ (ethyl group) and acac=(CH$_3$COCHCOCH$_3$)— (acetylacetonate) in their monomeric or dimeric form;

or
the tungsten precursor is selected from the following compounds: W(OEt)$_5$, W(OEt)$_6$, W(=O)(OEt)$_4$, W(=S)(OEt)$_4$, W(=S)(SEt)$_4$, W(=O)$_2$(OEt)$_2$, W(OC$_6$H$_5$)$_6$, W(SEt)$_5$, W(SEt)$_6$, W(OEt)$_4$(SEt), W(OEt)$_3$(SEt)$_2$, W(OEt)$_2$(SEt)$_3$, W(OEt)(SEt)$_4$, W(=O)(OEt)$_3$(acac) with Et=CH$_2$CH$_3$ (ethyl group) and acac=(CH$_3$COCHCOCH$_3$)— (acetylacetonate), in their monomeric or dimeric form.

15. The process as claimed in claim 14, wherein the surface density which corresponds to the amount of molybdenum Mo atoms or of tungsten W atoms, deposited per unit surface area of support, is between 0.5 and 12 atoms of Mo or W per square nanometer of support.

16. The process as claimed in claim 14, wherein the molybdenum precursor is selected from the following compounds: Mo(OEt)$_5$, Mo(OEt)$_6$, Mo(=O)(OEt)$_4$, Mo(=S)(OEt)$_4$, Mo(=S)(SEt)$_4$, Mo(=O)$_2$(OEt)$_2$, Mo(OC$_6$H$_5$)$_6$, Mo(SEt)$_5$, Mo(SEt)$_6$, Mo(OEt)(SEt)$_4$, Mo(OEt)$_2$(SEt)$_3$, Mo(OEt)$_3$(SEt)$_2$, Mo(OEt)$_4$(SEt), Mo(=O)(OEt)$_3$(acac) with Et=CH$_2$CH$_3$ (ethyl group) and acac=(CH$_3$COCHCOCH$_3$)— (acetylacetonate) in their monomeric or dimeric form.

17. The process as claimed in claim 14, wherein the tungsten precursor is selected from the following compounds: W(OEt)$_5$, W(OEt)$_6$, W(=O)(OEt)$_4$, W(=S)(OEt)$_4$, W(=S)(SEt)$_4$, W(=O)$_2$(OEt)$_2$, W(OC$_6$H$_5$)$_6$, W(SEt)$_5$, W(SEt)$_6$, W(OEt)$_4$(SEt), W(OEt)$_3$(SEt)$_2$, W(OEt)$_2$(SEt)$_3$, W(OEt)(SEt)$_4$, W(=O)(OEt)$_3$(acac) with Et=CH$_2$CH$_3$ (ethyl group) and acac=(CH$_3$COCHCOCH$_3$)— (acetylacetonate), in their monomeric or dimeric form.

18. The process as claimed in claim 14, wherein the surface density which corresponds to the amount of molybdenum Mo atoms or of tungsten W atoms, deposited per unit surface area of support, is between 1 and 7 atoms of Mo or W per square nanometer of support.

19. The process as claimed in claim 14, wherein the molybdenum precursor is Mo(OEt)$_5$.

20. The process as claimed in claim 14, wherein the tungsten precursor is W(OEt)$_5$ or W(OEt)$_6$.

* * * * *